US012797180B2

(12) United States Patent
Supper et al.

(10) Patent No.: US 12,797,180 B2
(45) Date of Patent: Nov. 17, 2026

(54) METHOD OF MAKING A HIGHLY FLEXIBLE STENT GRAFT AND STENT GRAFT

(71) Applicant: Angiomed GmbH & Co. Medizintechnik KG, Karlsruhe (DE)

(72) Inventors: Wolfgang Supper, Karlsruhe (DE); Martin Bauer, Karlsruhe (DE)

(73) Assignee: Angiomed GmbH & Co. Medizintechnik KG, Karlsruhe (DE)

( * ) Notice: Subject to any disclaimer, the term of this patent is extended or adjusted under 35 U.S.C. 154(b) by 701 days.

(21) Appl. No.: 18/022,726

(22) PCT Filed: Aug. 24, 2020

(86) PCT No.: PCT/EP2020/073644
§ 371 (c)(1),
(2) Date: Feb. 22, 2023

(87) PCT Pub. No.: WO2022/042820
PCT Pub. Date: Mar. 3, 2022

(65) Prior Publication Data

US 2023/0310141 A1 Oct. 5, 2023

(51) Int. Cl.
*A61F 2/91* (2013.01)
*A61F 2/06* (2013.01)
(Continued)

(52) U.S. Cl.
CPC .......... *A61F 2/07* (2013.01); *A61F 2002/072* (2013.01); *A61F 2230/0091* (2013.01); *A61F 2240/001* (2013.01)

(58) Field of Classification Search
None
See application file for complete search history.

(56) References Cited

U.S. PATENT DOCUMENTS 5,474,089 A * 12/1995 Waynant .................. A61F 6/20 128/842
6,254,632 B1 * 7/2001 Wu ........................ A61F 2/915 623/1.15
(Continued)

FOREIGN PATENT DOCUMENTS

EP 0971642 A1 1/2000
WO 9827894 A1 7/1998
(Continued)

OTHER PUBLICATIONS

PCT/EP2020/073644 filed Aug. 24, 2020 International Search Report and Written Opinion dated May 21, 2021.

*Primary Examiner* — Ann Hu
(74) *Attorney, Agent, or Firm* — Rutan & Tucker LLP

(57) ABSTRACT

The present invention relates to a method of making a highly flexible stent graft (100), the method comprising: providing a stent graft having a first and a second longitudinal end and a lumen extending longitudinally therethrough, the stent graft comprising a base stent (10), the base stent having a first covering material (14) provided on the inside of the base stent so as to line the lumen and a second covering material (12) provided on the outside of the base stent, locally ablating the second covering material without puncturing the first covering material to thereby increase the flexibility of the stent graft.

7 Claims, 1 Drawing Sheet

(51) Int. Cl.
*A61F 2/07* (2013.01)
*A61F 2/89* (2013.01)

(56) References Cited

U.S. PATENT DOCUMENTS

| | | | | |
|---|---|---|---|---|
| 8,591,568 | B2 * | 11/2013 | Molaei | A61L 31/022 623/1.48 |
| 9,259,339 | B1 * | 2/2016 | Yan | A61F 2/89 |
| 2001/0032009 | A1 | 10/2001 | Layne et al. | |
| 2002/0065553 | A1 * | 5/2002 | Weber | A61F 2/91 623/1.46 |
| 2004/0004063 | A1 * | 1/2004 | Merdan | B23K 26/16 219/121.67 |
| 2004/0079737 | A1 * | 4/2004 | Pinchasik | B23K 26/22 219/160 |
| 2005/0188921 | A1 * | 9/2005 | Malone | A61L 29/16 118/715 |
| 2006/0051522 | A1 * | 3/2006 | Talton | A61L 27/28 118/723 R |
| 2006/0287706 | A1 * | 12/2006 | Olsen | B23K 26/38 623/1.15 |
| 2007/0208421 | A1 * | 9/2007 | Quigley | A61F 2/07 623/1.44 |
| 2008/0312727 | A1 * | 12/2008 | Blank | B23K 26/38 623/1.2 |
| 2011/0307050 | A1 * | 12/2011 | Harrington | A61F 2/90 264/400 |

FOREIGN PATENT DOCUMENTS

| | | | | |
|---|---|---|---|---|
| WO | WO-03075797 | A2 * | 9/2003 | A61F 2/89 |
| WO | WO-03083458 | A2 * | 10/2003 | G01N 21/552 |
| WO | WO-2006065356 | A1 * | 6/2006 | A61M 25/0009 |
| WO | WO-2011008897 | A2 * | 1/2011 | A61P 9/10 |
| WO | WO-2017173366 | A1 * | 10/2017 | A61F 2/91 |
| WO | WO-2022031235 | A1 * | 2/2022 | B22F 5/106 |

* cited by examiner

METHOD OF MAKING A HIGHLY FLEXIBLE STENT GRAFT AND STENT GRAFT

PRIORITY

This application is a U.S. national stage of International Application No. PCT/EP2020/073644, filed Aug. 24, 2020, which is incorporated by reference in its entirety into this application.

TECHNICAL FIELD

The present invention concerns a method of making a highly flexible stent graft. It also concerns a stent graft that is manufacturable using such a method.

TECHNICAL BACKGROUND

Covered stents, which are also known as stent grafts, are used in a variety of surgical applications such as in endovascular aneurysm repairs, in the treatment of stenosis in vascular grafts and also as fistulas used for hemodialysis. Such stent grafts generally comprise a stent (which is often called a "base stent") that has a tubular shape with a lumen extending between two longitudinal ends.

The inner side of the base stent, that is, the side facing the lumen, is covered with a first layer of a graft material such as ePTFE. The outer side of the base stent is covered with a second layer of a graft material (which, again, is often ePTFE). Other biocompatible graft materials such as FEP can also be used. In such a stent graft, the base stent, which is frequently made of a shape memory alloy such as nitinol, defines the overall shape of the stent graft as such. The first and second layers of graft material lead to the stent graft as a whole having the shape of a tube so that blood will flow through it without significantly leaking through the walls of the stent graft.

With stent grafts (as well as stents), it is common that their flexibility needs to be rather high. This is because they need to be implanted via the often tortuous blood vessels inside a patient's body so that it is desired that the stents are flexible already during delivery (that is, before they are expanded). However, even after delivery when the stent grafts are placed at their intended destination in a patient's body, a high flexibility is desirable since it improves the compliance of the stent graft with the patient's body: too stiff a stent graft stiffens the blood vessel it is implanted in. Further, such a stent graft can give rise to complications at the junctions between the stent graft and the blood vessel. With a more flexible stent graft, the blood vessel does not respond as strongly to the implantation of the stent graft, and the stent graft also adapts to the blood vessel's anatomy more easily.

Additionally, it is also generally desired to reduce the delivery profile of stent grafts so that they can be delivered through narrow blood vessels. Yet, on the other hand, the stent graft should be made of a sufficiently strong material to prevent it from collapsing post-implantation.

To achieve such purposes, it is frequently attempted to reduce the wall thickness of the base stent or to reduce the thickness of the ePTFE covering layers, which leads to a higher degree of flexibility and to a reduced delivery profile. Additionally, more flexible or thinner covering materials are used, or the outer ePTFE layer is not formed as a single integral layer but as a ribbon that is wrapped around the base stent in the form of a helix with gaps between individual windings of the helix. It has also been attempted to make the base stent itself more flexible.

However, such arrangements are difficult to assemble since the second covering needs to be accurately aligned relative to the base stent. If a misalignment occurs, it is often the case that the stent graft needs to be discarded since it would not be acceptable to implant it in a patient.

It is additionally the case that the process of manufacturing partially covered stent grafts is rather complex. In the prior art processes of assembling such a stent graft, as a first step, an inner ePTFE layer as the first covering material is arranged on an assembly mandrel. Subsequently, a base stent is arranged on top of the inner ePTFE layer. In doing so, it needs to be made sure that the stent frame retains its shape. In practice, this is often difficult to achieve since such a base stent is generally highly flexible and can thus be easily deformed, misaligned, twisted, elongated and/or compressed. Accordingly, such an arrangement process is difficult to implement and requires a significant amount of skill.

Subsequently, the outer ePTFE layer forming the second covering material has to be arranged over the base stent. Of note, the base stent must not be misaligned or deformed during this arrangement process of the outer ePTFE layer. Given the need to avoid any distortions of the underlying base stent, also this step requires a great degree of care and skill.

In that respect, it is to be noted that, in order to provide the outer ePTFE layer, it is not necessary to use a single closed outer layer. Rather, it is possible to use individual wires or ribbons of ePTFE that can be wound around the base stent. Those ribbons/wires allow for a movement of the base stent sections during stent graft delivery which gives better bending flexibility. On the other hand, this step of laying the outer ePTFE layer requires the use of a complicated winding equipment to make sure that the ribbons/wires do not fall between the stent frame gaps during their winding processes as this would disarrange the base stent structure.

Subsequently, tapes and other layers are wound around the entire assembled stent graft structure prior to sintering to hold the stent graft structure in place during sintering. Again, it needs to be made sure that no relative movement of the inner arrangement of the base stent and of the inner and outer ePTFE layers occurs. Subsequently, the arrangement is heat treated so as to sinter it. Afterwards, the stent graft is unpacked, and the stent graft ends are trimmed. It is important that during all of those assembly steps, one is very careful as the outside ePTFE layer can move uncontrollably into the stent free gaps which are needed to have a flexible stent arrangement. If such an undesired movement occurs, it often happens that the stent graft itself is unfit for implantation and thus needs to be discarded.

SUMMARY OF THE INVENTION

The present inventors have realised that there are ways in which the previously described method can be optimised. In particular, they have realised that the way of covering the base stent can be improved so that the whole assembly process can be simplified. Accordingly, an aim of the invention is to provide a method of making a stent graft that leads to a highly flexible stent graft which is also easier to implement and which leads to a reduced production of stent grafts that are deficient and thus need to be discarded.

The invention is defined by independent method claim 1. Embodiments are defined in the dependent claims.

According to the invention, the method of making a highly flexible stent graft involves providing a stent graft having a first and a second longitudinal end and a lumen extending longitudinally therethrough. This stent graft comprises a base stent which could be made of a material such as nitinol. In embodiments, the base stent is self-expanding. In some embodiments, the base stent self-expands at around body temperature (i.e. around 37° C.). It is also conceivable that a balloon expandable base stent is used instead of a self-expanding base stent.

The base stent has a first covering material provided on the inside of the base stent so as to provide a lining for the lumen to allow blood to flow therethrough. It has a second covering material provided on the outside of the base stent. The first and the second covering material could, for example, be ePTFE. However, other biocompatible coating materials such as FEP are also envisaged. Subsequently, the second covering material is locally ablated (in embodiments by heat) without puncturing the first covering material. This localized ablation increases the flexibility of the stent graft.

By providing first a stent graft that is covered both on the inside and on the outside and by only subsequently ablating the second, outer covering material, a highly flexible stent graft is provided. This is because due to the second covering material being at least partially ablated, the thickness of the material of the stent graft is reduced. Further, since the final shape of the covering provided by the second covering material is achieved by means of the local ablation, one does not need to have a complicated procedure in place for arranging the second covering material on the base stent already in its final shape. This simplifies the manufacturing process.

Further, the inventive method of making a stent graft can be built on previous methods of making stent grafts that are covered in their entirety. It is only after one has applied the second covering material that the process needs to be modified since the second covering material is then to be partially removed. Therefore, for significant parts of the process, one can use well-established and well-characterized methods of manufacturing such stent grafts and only add on a step of ablating the second covering material towards the end.

With the method that is described above, a great degree of flexibility in the design of the outer surface can be achieved

- one can have helices at different pitches which follow or do not follow a base stent helix, and one can adjust the degree of covering rather flexibly. Additionally, one is not constrained to helical designs of the second covering material
- one could, for example ablate the second covering material to create discrete and approximately circular holes in the second covering material. One can also have a second covering material that covers the longitudinal and/or circumferential connectors of the base stent. It would be an option to write, for example, manufacturer and brand names on the stent graft by means of a carefully controlled ablation of the second covering material. Generally speaking, one can obtain, using CAD/CAM and/or Finite Element Analysis, a desired outer surface shape for the stent graft so as to have particular mechanical characteristics and then ablate the second covering material accordingly.

In embodiments, the second covering material is ablated by applying heat. The application of heat can be done using a variety of methods. Whilst the application of heat using a laser will be discussed subsequently, it is also conceivable that the heat is supplied by heat conduction, for example by means of holding a warm object against the stent graft. Alternative ways such as a focused flow of hot air are also conceivable. Apart from applying heat, it would also be an option to use mechanical ablation processes for ablating the second covering material, for example by using a milling or grinding technique. The application of heat is such that the second covering material is vaporized locally.

It is to be noted that whilst in embodiments, the first and second covering materials are provided in a tube form or in a sheet form, in other embodiments, electrospinning can be used to provide them. Further, whilst in some embodiments, ePTFE (expanded polytetrafluoroethylene) is used, other materials such as PET (polyethylene terephthalate, sometimes sold under the name "Dacron") can also be used. Put more generally, the material compositions of the first and second covering materials are not limiting, and the improvement in flexibility happens regardless of the materials used for the first and second covering materials.

In one embodiment, the second covering material is ablated so as to locally uncover the base stent. That is, when the material is ablated, the base stent gets at least partially exposed to the outside. When the base stent is uncovered locally, the second covering material is completely removed at those points. This leads to a significant increase in the flexibility of the stent graft. It also means that, if heat is applied, the heat that is applied can be conducted to the base stent itself. Since that stent is typically made of metal and therefore has a good heat conductivity, such a method of making a highly flexile stent graft avoids applying unnecessary heat to the first covering material. This avoids damaging the first covering material. Accordingly, such a method is more reliable.

In other embodiments, the laser only locally thins the second covering material. That is, the material of the base stent is not uncovered. This method retains the second covering material without creating "holes" in it, which can be advantageous in some applications.

In embodiments, the second covering material has, prior to the local ablation, a thickness within the range of 0.02-0.15 mm. Having such a thickness leads to a stent graft that is on the other hand highly flexible whilst also being resilient.

In some specific embodiments, where the second covering material has a thickness within the range of 0.02-0.15 mm, the second covering material is locally thinned by at least 50% of the thickness of the second covering material. This ensures that the thinned portions are sufficiently thinned so as to provide a highly flexible stent graft.

In one embodiment, the heat is applied by means of a laser. Such lasers can be polymer evaporation lasers, for example carbon dioxide lasers. Lasers can be easily manipulated, which leads to a method of making a highly flexible stent graft that is comparatively easy to control.

In embodiments, the laser is applied so as to graze the stent graft. That is, the laser is applied so that it is tangentially incident on the outer surface of the stent graft in a way that is comparable to a lathe in a turning workshop. Such a way of applying a laser allows for accurate controlling since one does not need to focus the laser so as to control its position of application. Rather, since one generally knows the direction of propagation of a laser rather well, and since a laser beam is generally strongly collimated, the spatial extent of the beam is generally well known. This then means that one can comparatively easily control the position where the laser is applied to the second covering material, which, in turn, means that one can comparatively easily control how deeply the second covering material is ablated.

In an alternative embodiment, the laser is applied so as to impinge perpendicularly onto the second covering material.

In that way, the whole of the laser power can be applied to the stent graft, which reduces the time that is needed for ablating the second covering material.

In yet another alternative embodiment, the laser is applied so as to impinge at an angle between 30° and 60° relative to the lengthwise direction of the stent graft onto the second covering material. In such a way of having the laser shine onto the second covering material, the evaporated second covering material will be largely blown away from the stent graft by the evaporation gases, which improves the quality of the thus produced stent graft.

In embodiments, the second covering material is ablated so as to cut a helical pattern into the second covering material, with the helix extending along the axial direction of the stent graft. Having such a helical pattern is particularly advantageous as it leads to the flexibility of the whole of the stent graft being increased along the whole length over which the helical pattern is applied. With a ring-like pattern, with the rings being separated by parts of the second covering material, there would always be a certain degree of unevenness in the flexibility of the stent graft. On the other hand, such rings might be beneficial for other mechanical advantages during the medical procedure (e.g. device coupling, space for sensors).

In a second aspect of the present invention, a stent graft for use in endovascular surgery is claimed. This stent graft has a base stent that has a proximal end a distal end and a lumen extending longitudinally therethrough. A first covering material is provided on the inside of the base stent so as to line the lumen and so as to provide a tube that allows for bodily liquids to flow therethrough without significantly leaking to the outside. A second covering material is provided on the outside of the base stent and is bonded to the first covering material and/or the base stent. The second covering material is provided only on part of the outside of the base stent so as to form a helical structure. Having such a stent graft is advantageous in that the stent has a high degree of flexibility and uniformity. Embodiments of such a stent graft can be manufactured using the previously described inventive method.

In embodiments of the inventive stent graft, there is a ring-portion at one longitudinal end of the stent graft which has an uncovered portion of the base stent by the selective ablation of the second covering material whilst retaining the first covering material. In some embodiments, a ring-portion can be provided at both longitudinal ends. Such ring-portions are advantageous in that they save material and thus reduce the profile in the delivery catheter. They also make it easier to load the stent graft into such a delivery catheter.

DETAILED DESCRIPTION OF THE DRAWINGS

Figure 1:
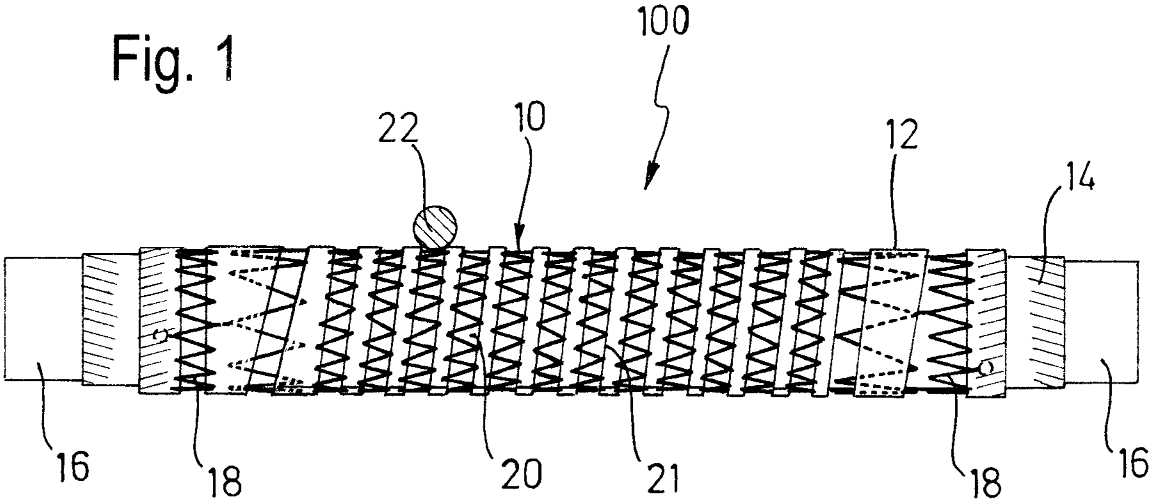
FIG. 1 shows a manufactured stent graft according to one embodiment of the present invention.
Figure 2:
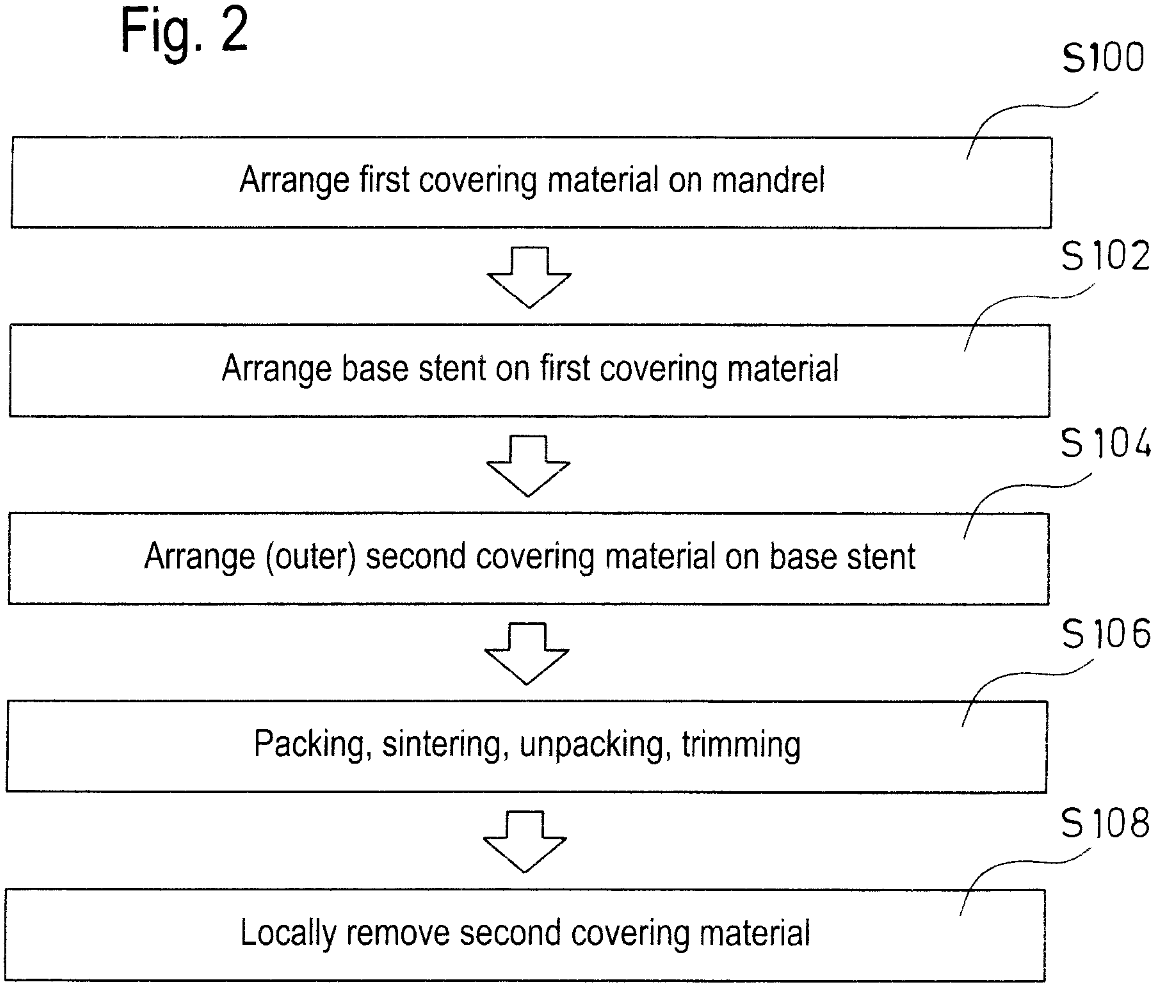
FIG. 2 shows a method of manufacturing a stent graft according to one embodiment of the present invention.

A method of manufacturing a stent graft according to the present invention will now be described with reference to FIGS. 1 and 2.

In a first step (Step S100), an assembly mandrel 16 is provided. On that assembly mandrel 16, a first covering material 14, which could be ePTFE, is arranged. This ePTFE material can be provided in a sheet form. A sheet form, rather than a strip form, is advantageous in that no winding process is required: a winding process would require a great degree of precision since one has to ensure that adjacent windings abut against each other on the mandrel without overlapping in the radial direction. It is also possible to use a prefabricated tubular material instead of a sheet or a strip material.

Subsequently (Step S102), a base stent 10 is arranged on the first covering material 14. In that step, it is important to ensure that the base stent 10 retains its shape and is thus not stretched or otherwise deformed. The base stent 10 can be made of self-expanding material, such as nitinol, such that the base stent self-expands at around body temperature after being navigated to the desired location and deployed from the delivery catheter.

Subsequently, in step S104, a second covering material 12 is arranged on the base stent 10. The second covering material 12 could also be ePTFE that is provided in a sheet form. It would also be possible to use a single layered tubing for the second covering material 12. The thickness of the first and/or second covering material 14, 12 falls within the range of from 0.02-0.15 mm.

Afterwards, in step S106, the arrangement is packed and then sintered so that the first and second covering materials 12, 14 and the base stent 10 are integrated so as to adhere to one another. Afterwards, the stent graft is unpacked.

After that step S106, in the next step S108, the second covering material 12 is locally ablated so that a discrete portion of the base stent is uncovered by the second covering material. It is also envisaged that the second covering material 12 is only made thinner, without being entirely ablated. The ablation of the second covering material can be accomplished by using a laser, such as a carbon dioxide polymer evaporating laser 22. The carbon dioxide polymer evaporating laser 22 is applied to the outside layer of the stent graft 100 in a controlled manner so as to locally remove by vaporizing the second covering material 12. In the configuration that is shown in FIG. 1, the laser 22 is applied in a grazing manner so that it would, in the context of that drawing, be propagating along a direction that is perpendicular to the sheet on which the drawing is printed. Of course, this is just exemplary, and other angles of propagation are possible as discussed above. Afterwards, the stent graft 100 is removed from the mandrel 16 and is trimmed if necessary.

By this ablation, gaps 20 in the second covering material 12 are provided that have the form of a spiral 21. The spiral 21 ends in two ring-shaped gaps 18 at either longitudinal end of the stent graft 100.

The invention claimed is:

1. A method of making a highly flexible stent graft, the method comprising:

providing a stent graft having a first longitudinal end and a second longitudinal end and a lumen extending longitudinally therethrough, the stent graft comprising a base stent, the base stent having a first covering material provided on an inside of the base stent so as to line the lumen and a second covering material provided on an outside of the base stent, and locally ablating the second covering material without puncturing the first covering material to thereby increase flexibility of the stent graft, wherein locally ablating occurs by means of applying heat to the second covering material, wherein the heat is applied by means of a laser, the laser being applied so as to impinge at an angle between 30° and 60° onto the second covering material.

2. The method according to claim 1, wherein the second covering material is ablated so as to locally uncover the base stent.

3. The method according to claim 1, wherein the second covering material is ablated so as to be locally thinned without locally uncovering the base stent.

4. The method according to claim 1, wherein the second covering material has, prior to locally ablating, a thickness within a range of 0.02 to 0.15 mm.

5. The method according to claim 3, wherein the second covering material is locally thinned by at least 50% of a maximum thickness of the second covering material.

6. The method according to claim 1, wherein the laser is applied so as to graze the stent graft.

7. The method according to claim 1, the second covering material being ablated so as to cut a helical pattern into the second covering material, with the helical pattern extending along an axial direction of the stent graft.

* * * * *